(12) United States Patent
Fischer et al.

(10) Patent No.: US 10,830,718 B2
(45) Date of Patent: Nov. 10, 2020

(54) SENSOR FOR DETECTING IMMERSION IN F.O.G. OR WATER

(71) Applicant: Thermaco, Inc., Asheboro, NC (US)

(72) Inventors: Jan Robin Fischer, Elon, NC (US); Bruce W. Kyles, Asheboro, NC (US); William C. Batten, Asheboro, NC (US)

(73) Assignee: Thermaco, Inc., Asheboro, NC (US)

( * ) Notice: Subject to any disclaimer, the term of this patent is extended or adjusted under 35 U.S.C. 154(b) by 0 days.

(21) Appl. No.: 16/031,245

(22) Filed: Jul. 10, 2018

(65) Prior Publication Data

US 2019/0137423 A1 May 9, 2019

Related U.S. Application Data

(60) Provisional application No. 62/565,541, filed on Sep. 29, 2017, provisional application No. 62/530,437, filed on Jul. 10, 2017.

(51) Int. Cl.
*G01N 25/18* (2006.01)
*C02F 1/40* (2006.01)
(Continued)

(52) U.S. Cl.
CPC ............ *G01N 25/18* (2013.01); *B01D 17/00* (2013.01); *B01D 17/0208* (2013.01); *B01D 17/12* (2013.01); *C02F 1/40* (2013.01); *G01F 23/22* (2013.01); *G01N 33/1833* (2013.01); *H05K 1/09* (2013.01); *H05K 1/181* (2013.01); *H05K 5/064* (2013.01); *C02F 2103/32* (2013.01);
(Continued)

(58) Field of Classification Search
CPC . H05K 2201/10196; H05K 2201/0338; H05K 2201/10022; H05K 2201/10151
See application file for complete search history.

(56) References Cited

U.S. PATENT DOCUMENTS 3,025,962 A    9/1958 Williams .................. 210/86
3,923,655 A   12/1975 McKinney ................ 210/83
(Continued)

FOREIGN PATENT DOCUMENTS

| CN | 202748633 | 2/2013 | ........... B01D 17/032 |
| RU | 2336502 | 3/1992 | ............. G01F 23/22 |
| WO | WO 2017/035220 | 3/2017 | ............. B01D 17/02 |

OTHER PUBLICATIONS

Search Report of Counterpart PCT Application PCT/US 2018/041422.
(Continued)

*Primary Examiner* — Richard C Gurtowski
(74) *Attorney, Agent, or Firm* — MacCord Mason PLLC

(57) ABSTRACT

An apparatus for discriminating between liquids having differing thermal conductivities includes a thermally conductive substrate, a resistor and a thermistor mounted to the thermally conductive substrate. Two leads on the resistor enable a current to be passed through the resistor to generate heat, and two leads on the thermistor enable a current to be passed through the thermistor to generate a datum indicative of thermistor temperature. An electrical insulator encapsulates the resistor, the thermistor and part of the thermally conductive substrate. A remainder of the thermally conductive substrate may extend beyond the electrical insulator to provide a thermal path from the resistor and thermistor to a liquid in which the apparatus may be immersed.

20 Claims, 13 Drawing Sheets

(51) Int. Cl.
*B01D 17/00* (2006.01)
*B01D 17/02* (2006.01)
*G01F 23/22* (2006.01)
*B01D 17/12* (2006.01)
*G01N 33/18* (2006.01)
*H05K 1/09* (2006.01)
*H05K 1/18* (2006.01)
*H05K 5/06* (2006.01)
*C02F 103/32* (2006.01)

(52) U.S. Cl.
CPC .. *C02F 2209/42* (2013.01); *H05K 2201/0338* (2013.01); *H05K 2201/10022* (2013.01); *H05K 2201/10151* (2013.01); *H05K 2201/10196* (2013.01)

(56) References Cited

U.S. PATENT DOCUMENTS

| | | | |
|---|---|---|---|
| 4,832,711 A | 5/1989 | Christel, Jr. et al. ............. 55/20 |
| 4,972,709 A | 11/1990 | Bailey, Jr. et al. ............. 73/290 |
| 5,705,055 A | 1/1998 | Holloway, Jr. et al. ........ 210/86 |
| 5,946,967 A | 9/1999 | Russell | |
| 6,014,076 A | 1/2000 | Luzzader ...................... 340/521 |
| 6,108,212 A * | 8/2000 | Lach ................... H01L 21/4853 174/255 |
| 6,251,286 B1 | 6/2001 | Gore ............................. 210/744 |
| 6,619,118 B1 | 9/2003 | Keck | |
| 6,879,935 B2 | 4/2005 | Keck | |
| 7,828,960 B1 | 11/2010 | Batten et al. ................... 210/86 |
| 7,854,051 B2 | 12/2010 | Batten et al. ................ 29/403.3 |
| 9,095,162 B2 | 4/2015 | Xia .......................... A23L 1/015 |
| 9,139,457 B2 | 9/2015 | Hatten ...................... C02F 1/78 |
| 2005/0109682 A1 | 5/2005 | Mazurek et al. ............... 210/86 |
| 2009/0071243 A1* | 3/2009 | Camp .................... G01F 1/696 73/204.23 |
| 2009/0159355 A1 | 6/2009 | Garwood et al. ............. 180/165 |
| 2009/0320265 A1 | 12/2009 | Batten et al. ................... 29/428 |
| 2011/0068060 A1 | 3/2011 | Hatten ......................... 210/739 |
| 2011/0232381 A1 | 9/2011 | Al-Absi et al. ................. 73/290 |
| 2012/0106112 A1* | 5/2012 | Knies ..................... H01L 24/97 361/783 |
| 2012/0221288 A1* | 8/2012 | Ioannidis ................ G01N 25/18 702/136 |
| 2015/0118373 A1 | 4/2015 | Xia ..................................... 1/15 |
| 2015/0293032 A1 | 10/2015 | Babichenko ..................... 21/94 |

OTHER PUBLICATIONS

Sensor Smartserv Grease Brochure, Intelligent Grease Management, p. 1-4.

VL53L1 a Flight Sense™ Product ST life. Augmented 2017 STMicroelectrionics p. 1-3.

VL53L0X World Smallest Time-of-Flight ranging and gesture detection senor ST life.augmented 2016 STMicroelectronics, p. 1-40.

* cited by examiner

Raw test curves for oil and water in similar ranges:

Readings from Figure 21 sensor

SENSOR FOR DETECTING IMMERSION IN F.O.G. OR WATER

BACKGROUND OF THE INVENTION

Oil, grease and solid waste contaminant removal or recovery systems are well known in the prior art. Over the past thirty years there has been a steady move towards requiring food handling facilities to have systems for servicing kitchen grease and solid waste bearing water flows. Sewer system lines can become clogged from the fats, oil and grease waste materials (hereinafter referred to as "F.O.G.") put into the sewer system from food handling facilities. This has led more and more sewer authorities to implement fats, oils and grease control programs. These programs regulate food handling facilities and the manner in which they process F.O.G.s. The object of many of these programs is to ensure that food handling facilities remove as much of the F.O.G. as possible from the effluent flow, thereby releasing only grey water to the sewer system.

Active separators remove F.O.G. from the effluent, typically by some skimming operation. Skimming when skimming is required and not skimming when it is not required has been an issue for the art. The traditional methodology is simply to use a timer that turns on the skimming apparatus at a certain time of day and runs it for a certain period, providing the user only with control as to the time of day and duration. For installations that have very regular schedules, this may be sufficient. However, for other installations that operate on less than a regular schedule, problems can arise. Schedule variations can be as simple as the differences between weekday and weekend operation. Also, for installations such as school cafeterias that do not operate during the summer, F.O.G. will not be added to the effluent during the summer, so there is not a reason to run the separator during the summer. Nonetheless, if the separator works on a daily schedule according to its timer, it will run even if there is no F.O.G. to be removed.

One of the downsides of this operation, besides the wasted energy of skimmer operation, is that when all of the F.O.G. is removed, the water becomes exposed. There may be food solids remaining in the water that are decomposing and off-gassing foul odors. If a F.O.G. mat is allowed to remain on the water, the odor is contained within the water. Also, humidity emanating from the water can rise into the electronics and provide a challenge to the longevity of the electronics.

Water and F.O.G. both dissipate (conduct) heat, but at different rates. By heating up a sensor unit and measuring how fast it gets hot one can measure how easily the heat is dissipated in the surrounding media. This heat dissipation rate can then be indicate the whether the sensor unit is in F.O.G. or water.

One device for making water or F.O.G. determinations using thermocouples is disclosed in U.S. Pat. No. 7,828,960, which issued Nov. 9, 2010, the entire disclosure of which is incorporated herein by reference. However, thermocouples can be expensive and provide other challenges. For example, the effluent in which the sensor is immersed can be corrosive, since it includes a wide range of items that are discharged through kitchen sinks, including cleaning agents and bleaches. The sensor must be able to withstand such corrosive attacks in order to give reliable information over time. Also, the kitchen effluent may have a range of temperatures, a range that can vary over time even for a single installation. When boiling water is a substantial part of the effluent, a temperature based sensor such as a thermistor will react differently than when a pitcher of ice water is drained. Practical applications may involve battery power, so reducing power consumption is preferred in order to lengthen battery life.

SUMMARY OF THE INVENTION

The present invention fulfills one or more of these needs in the art by providing an apparatus for discriminating between liquids having differing thermal conductivities. A thermally conductive substrate has a resistor mounted to it with two leads to enable a current to be passed through the resistor to generate heat. A thermistor is also mounted to the substrate with two leads to enable a current to be passed through the thermistor to generate a datum indicative of thermistor temperature. An electrical insulator encapsulates the resistor, the thermistor and part of the thermally conductive substrate. A remainder of the thermally conductive substrate may extend beyond the electrical insulator to provide a thermal path from the resistor and thermistor to a liquid in which the apparatus may be immersed in some embodiments.

In one embodiment the leads of the resistor and thermistor are electrically connected to electrically conductive regions of the thermally conductive substrate. One lead of the resistor and one lead of the thermistor may both be electrically connected to a common electrically conductive region of the thermally conductive substrate. That region may be connected to ground.

The substrate may be a printed circuit board with a metal face, such as copper. The copper may be coated with gold, particularly. The remainder of the thermally conductive substrate may extend beyond the electrical insulator. The electrical insulator may be a potting compound.

The leads of the thermistor may be connected to a data gathering unit that samples the data indicative of thermistor temperature over a period of at least forty seconds and computes a ratio of temperature rise. The denominator of the ratio is the temperature rise in the first twenty seconds and the numerator of the ratio is the temperature rise in the sampled period after the first twenty seconds.

A thermal paste may be located between the thermally conductive substrate and the resistor and thermistor.

The invention may also be considered as a separator for separating F.O.G. from an effluent that contains F.O.G. and water. The separator includes a tank, an inlet to the tank for receiving effluent that contains F.O.G. and water and an outlet to allow grey water to leave the tank, the tank having a size to enable stratification to form a layer of F.O.G. in the tank on top of water in the tank. A sensor apparatus is located at a location within the tank for discriminating between F.O.G. and water at the location in the tank. The sensor apparatus includes a thermally conductive substrate, a resistor mounted to the thermally conductive substrate with two leads to enable a current to be passed through the resistor to generate heat, and a thermistor mounted to the substrate with two leads to enable a current to be passed through the thermistor to generate a datum indicative of thermistor temperature. An electrical insulator encapsulates the resistor, the thermistor and at least part of the thermally conductive substrate. A remainder of the thermally conductive substrate may extend beyond the electrical insulator to provide a thermal path from the resistor and thermistor to a liquid in the tank. Differing voltages in the thermistor can be sensed to determine if the sensor apparatus is surrounded by air, F.O.G. or water.

The invention may also be considered as a method of discriminating between liquids having differing thermal conductivities. The method includes positioning a sensor at a location where it may be exposed to the liquids having differing thermal conductivities, the sensor including a thermal path from a heater and a thermistor. The thermal path may have a thermal conductivity comparable to copper. The method also includes applying heat to the sensor with the heater, reading data from the thermistor indicative of thermistor temperature repeatedly over a period of at least forty seconds, and computing a ratio of temperature rise, the denominator of the ratio being the temperature rise in the first twenty seconds of the data gathering period and the numerator of the ratio being the temperature rise in the data gathering period after the first twenty seconds. Alternatively, the computation may include taking an area under the curve of the temperature versus time. Alternately, the computation may include sampling a selected temperature rise to determine if the sensor is in one liquid or the other.

The liquids having differing thermal conductivities may be various liquids including lipids and water; petroleum oils and water; and concentrated alcohols and water.

BRIEF DESCRIPTION OF THE DRAWINGS

The invention will be better understood by a reading of the Detailed Description of the Examples of the Invention along with a review of the drawings, in which.

DETAILED DESCRIPTION OF EXAMPLES OF THE INVENTION

Figure 1:
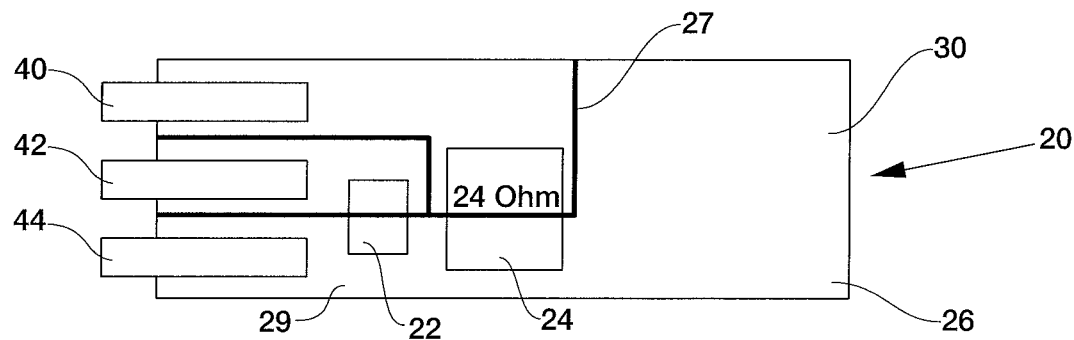
FIG. 1 is a top schematic view of a sensor in accordance with an embodiment of the invention before its encapsulation.
Figure 2:
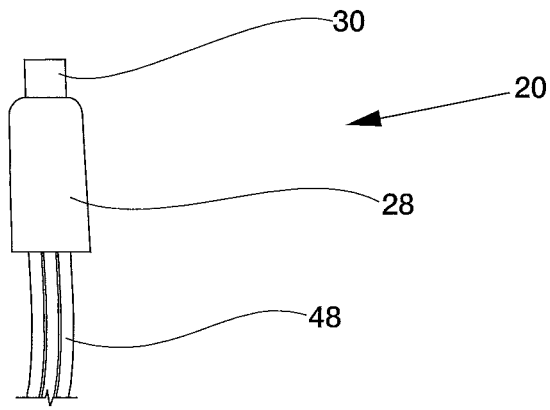
FIG. 2 is a perspective view of a sensor in accordance with an embodiment of the invention.
Figure 3:
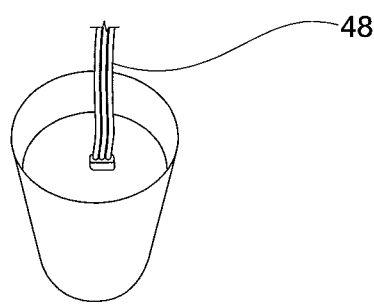
FIG. 3 is a perspective view of a sensor in accordance with an embodiment of the invention as immersed in a test liquid.
Figure 4:
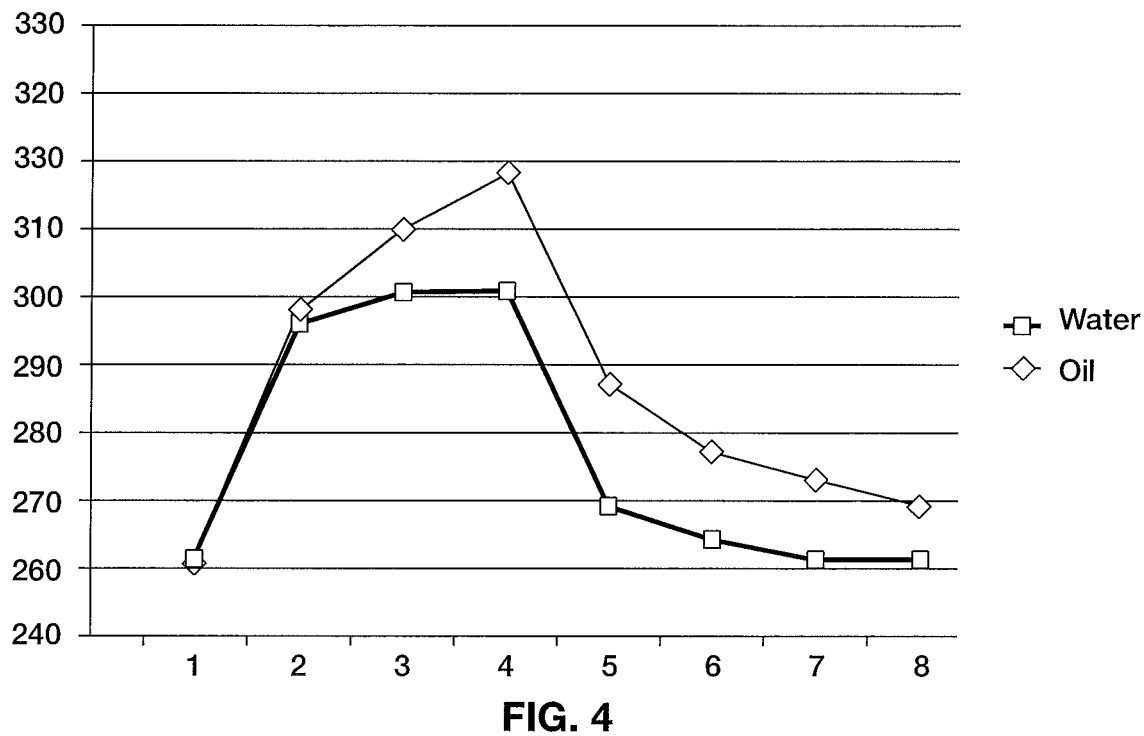
FIG. 4 is a graph of temperature rise over time for oil and water.
Figure 5:
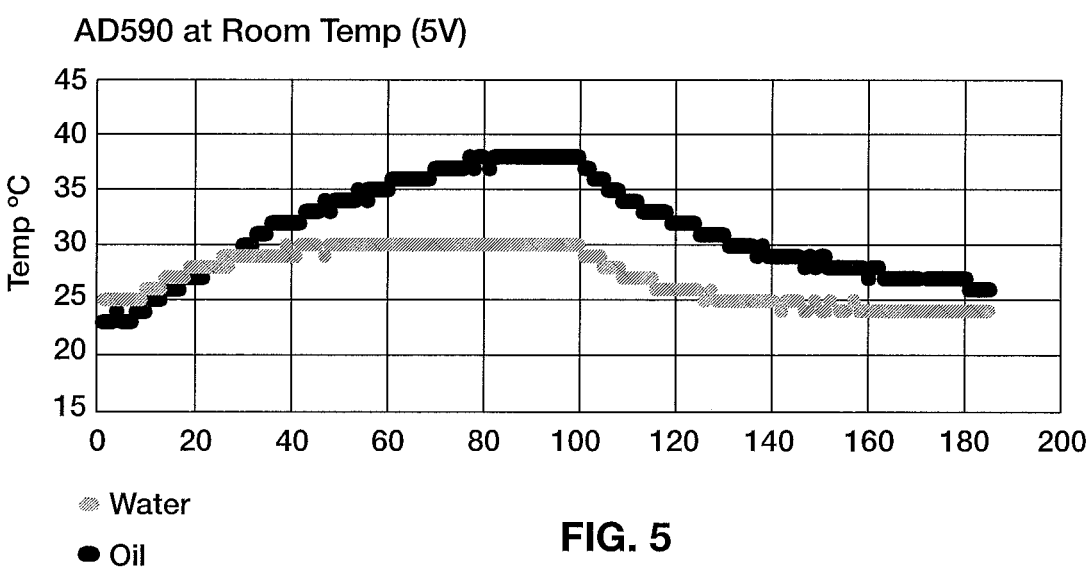
FIG. 5 is a graph of temperature rise over time for oil and water using a particular thermistor at a 5 volt heater voltage.
Figure 6:
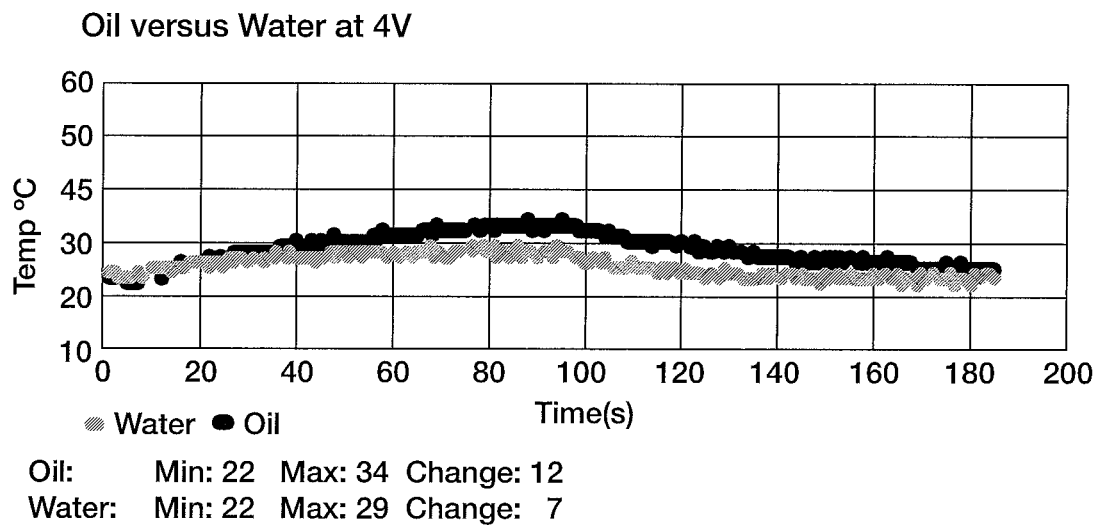
FIG. 6 is a graph of temperature rise over time for oil and water using a particular thermistor at a 4 volt heater voltage.
Figure 7:
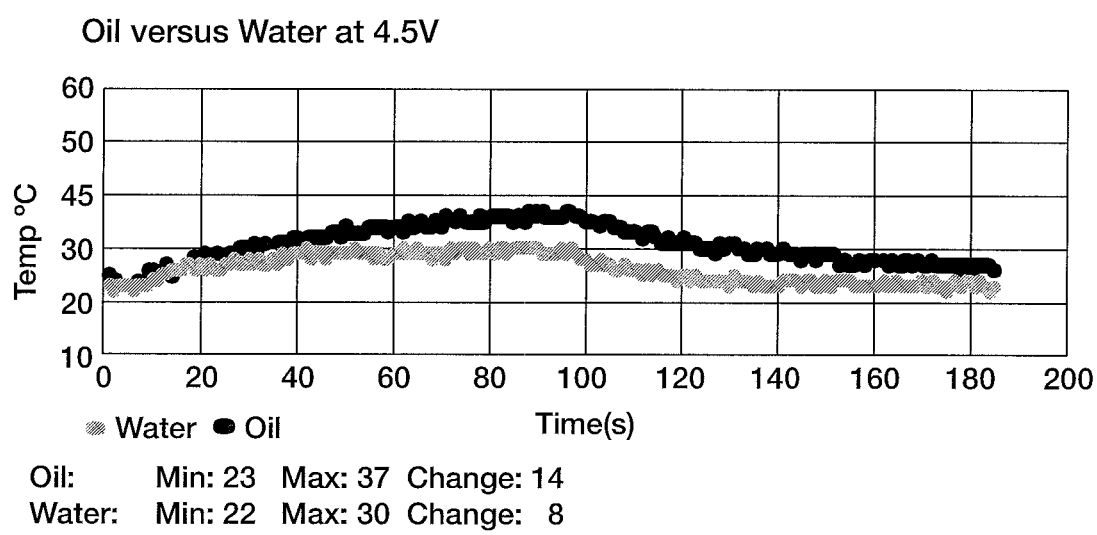
FIG. 7 is a graph of temperature rise over time for oil and water using a particular thermistor at a 4.5 volt heater voltage.
Figure 8:
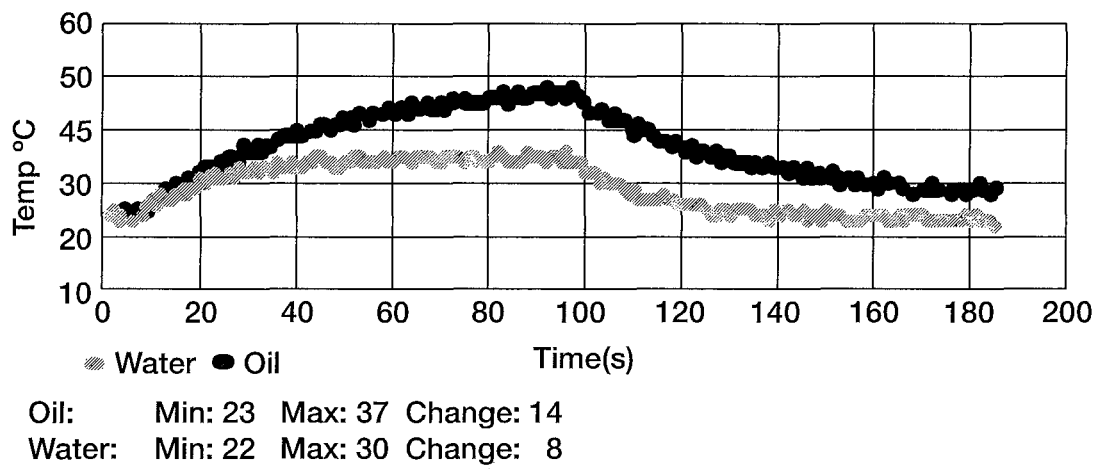
FIG. 8 is a graph of temperature rise over time for oil and water using a particular thermistor at a 6 volt heater voltage.
Figure 9:
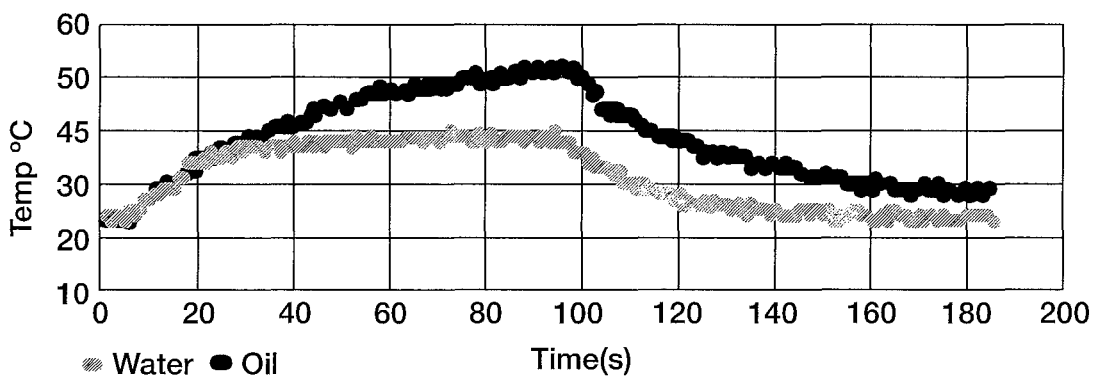
FIG. 9 is a graph of temperature rise over time for oil and water using a particular thermistor at a 7 volt heater voltage.
Figure 10A:
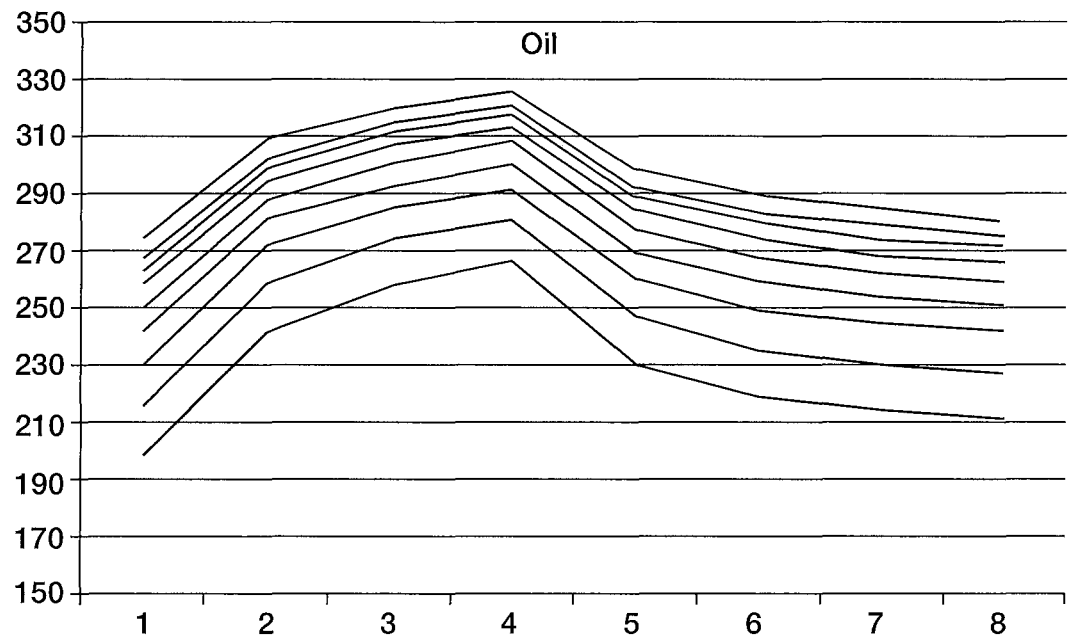
FIGS. 10A and 10B are raw data test curves for oil and water in similar temperature ranges.
Figure 10B:
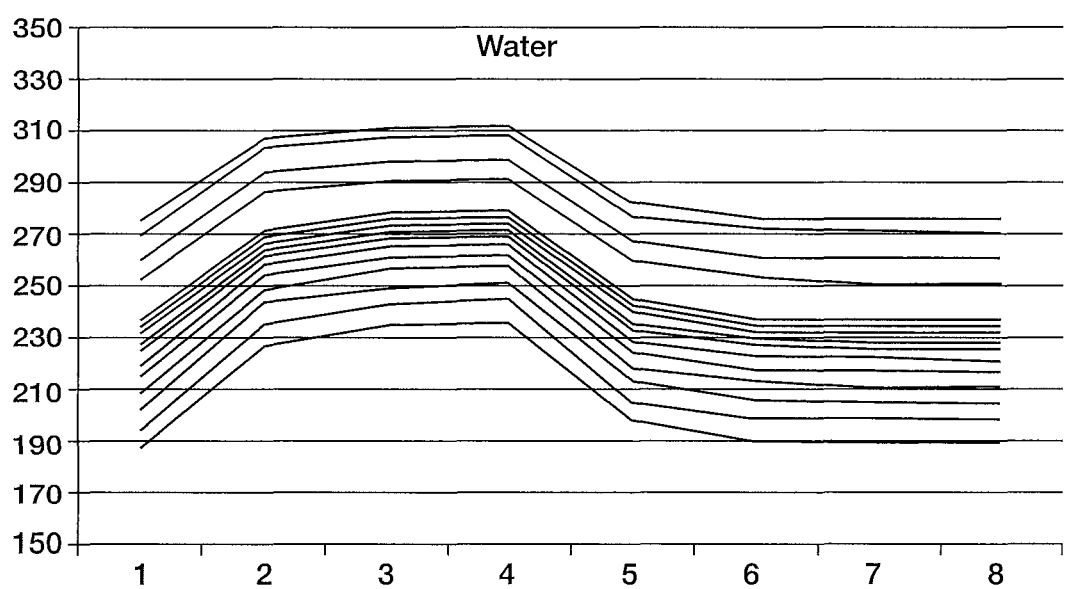
Figure 11:
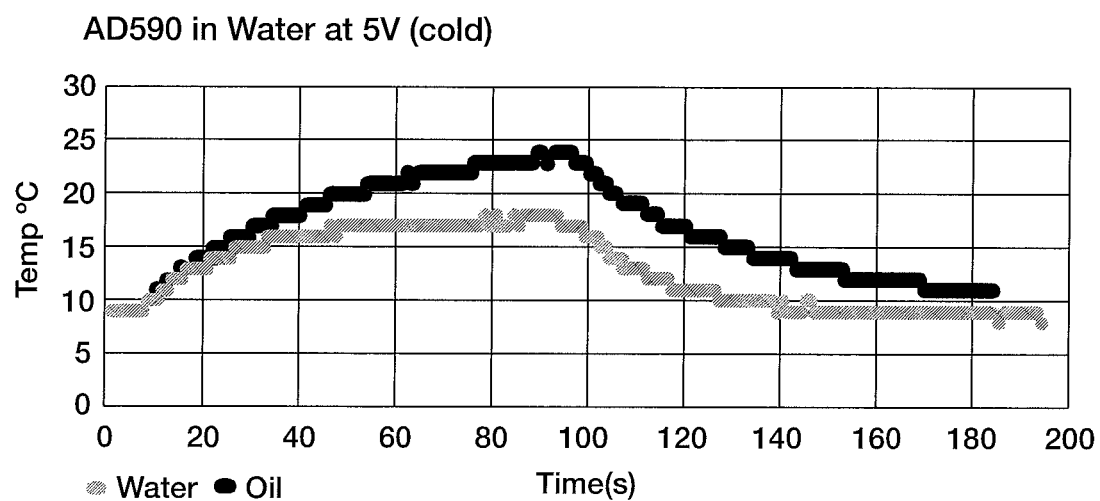
FIG. 11 is a graph of temperature rise over time for oil and water using a particular thermistor at a 5 volt heater voltage starting at a colder temperature.
Figure 12:
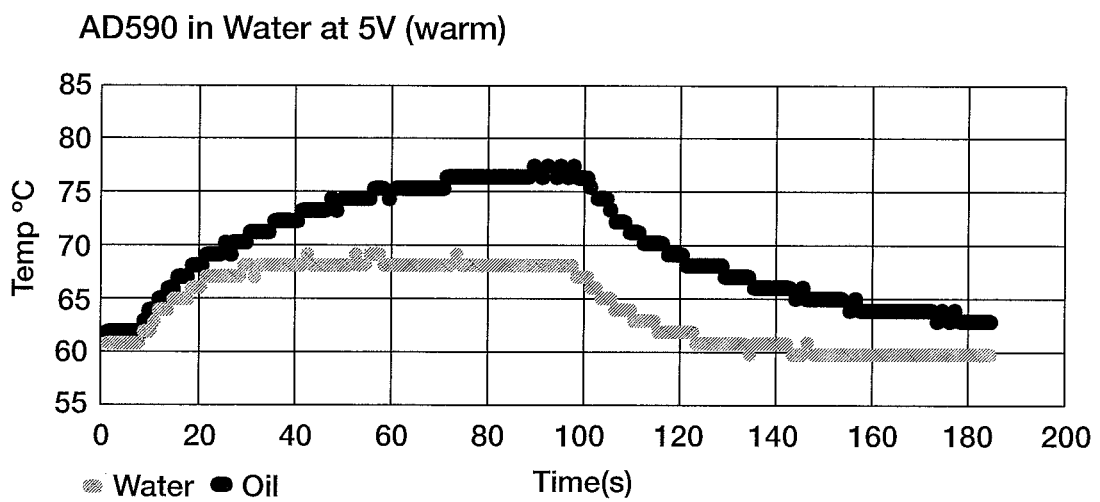
FIG. 12 is a graph of temperature rise over time for oil and water using a particular thermistor at a 5 volt heater voltage starting at a warmer temperature.
Figure 13:
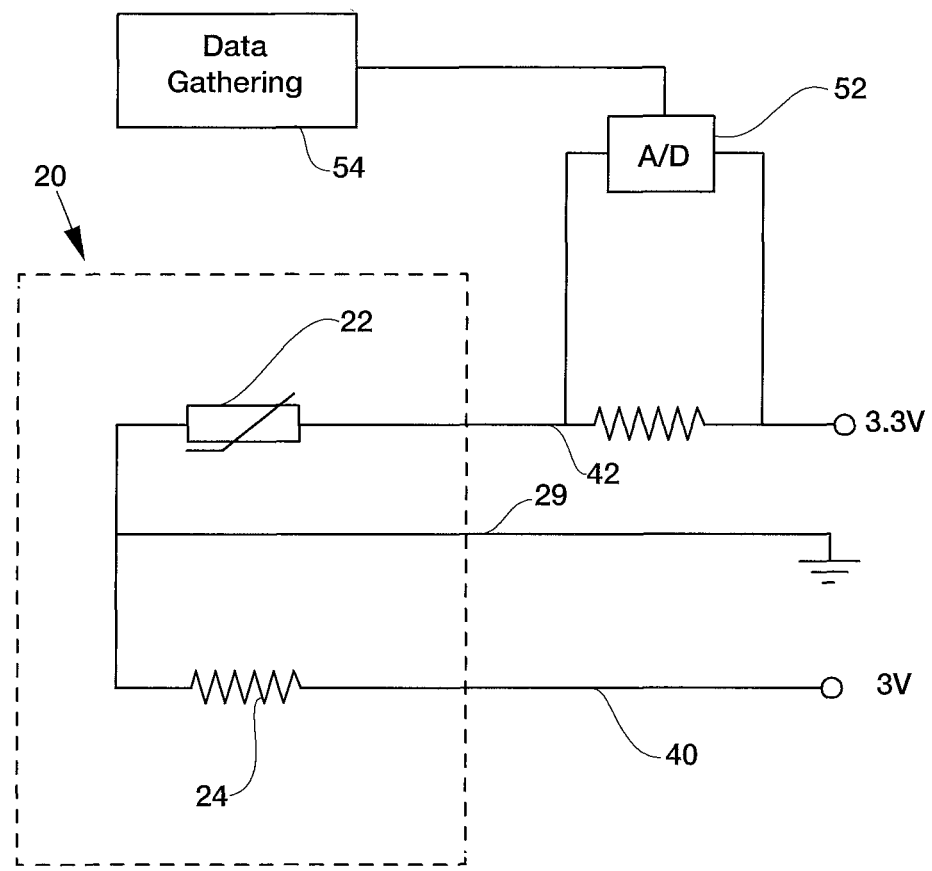
FIG. 13 is a schematic circuit diagram showing an embodiment of the sensor in a data-gathering mode.

As seen in FIGS. 1 and 13, a contact sensor 20 has a surface mounted resistor 24 and thermistor 22 on a small printed circuit board 26. The board 26 is shown with a top surface covered with copper. Etchings 27 break electrical conductivity between portions of the board where one of the leads of the resistor 24 and thermistor 22 are mounted. However, each of resistor 24 and thermistor 22 is attached to a zone 29 that can serve as a common or ground connection 44. Connector tabs 40, 42, and 44 enable connection to wires 48 shown in FIG. 2. Tab 40 is connected to a battery or other voltage source (not shown). Tab 42 is connected to data gathering equipment (not shown, but discussed below).

A potting compound 28 (seen in FIG. 2) covers the resistor and thermistor on the printed circuit board. A suitable potting compound is a potting epoxy. A heat sink segment 30 of the board is left exposed and not covered by the potting compound. In one embodiment the board 26 can use a 24 ohm resistor 24 run at 3V in order to generate the heat. The specific design of the thermistor 22 does not matter, as long as its range allows the reading of temperatures decently accurately over a large range of temperatures, ideally from just under the freezing point of water up to close to its boiling point.

A particular embodiment of the sensor uses an 8 pin AD590 Temperature Transducer (available from Analog Devices, One Technology Way, Norwood, Mass.) as the thermistor 22 and a 24 ohm resistor 24. Both have a layer of thermal paste between them and the copper on the printed circuit board to enhance thermal conductivity between them and the copper on the printed circuit board. They are glued to the copper using Loctite 401.

As seen in FIG. 13, the data gathering equipment 54 can use an Arduino ESP8266 WiFi Module attached to an analog-to-digital converter 52 that digitizes the signal on tab 42 transmitted on lead 48. The ESP8266 WiFi Module has integrated TCP/IP protocol stack that can give a microcontroller access to a WiFi network to communicate the data points over the internet to a data collection unit. In a test set-up the internet data collection unit used allows for a maximum of one data point every 15 seconds, so to ensure no data was lost, data was sent only every 20 seconds. Other data gathering systems can collect data at different rates. The algorithm was set to read an initial temperature, turn on the internal heating element (the resistor) and take a temperature reading every 20 seconds with the thermistor for a minute.

Afterwards the heating element was turned off and four additional readings were taken.

In operation, the sensor 20 will be immersed in a liquid mixture that includes liquids having differing thermal conductivities, particularly immiscible liquids that stratify, so that each liquid is more or less separated from the other. An example of such stratified liquid is an effluent containing F.O.G. and water that are separated in a grease interceptor or grease trap. The sensor may also be used in other applications, such as lipids and water, petroleum oils and water, concentrated alcohols and water, etc. The sensor gauges the relative thermal conductance of the media adjacent to the resistor-thermistor components section of the circuit. The sensor can discern between petroleum oil and water layers in a container used in industrial site for separating and capturing hydraulic oils spilled into an effluent stream.

An electrical voltage is applied to the leads of the resistor 24, causing it to generate heat that is conducted through the printed circuit board 26 and out the heat sink segment 30 into the surrounding liquid. Heat also can be conducted through the potting compound or other electrical insulator that is used to encapsulate the resistor and thermistor. Initially, much of the heat will be contained in the apparatus, but over time the surrounding liquid also heats up. However the rate of heating varies depending on which liquid surrounds the sensor 20. Water conducts heat better than F.O.G. does, so if the sensor is immersed in water, the heat conducts further and faster than if the sensor is immersed in F.O.G. Since the heat moves away from the sensor faster in water than it does in F.O.G., the temperature rises faster in F.O.G. than in water. (If the sensor is in air, the heat conducts much more slowly, so the temperature rises faster than in water or F.O.G.) This different rate of rise of temperature can be measured using the thermistor 22. However, reading that temperature rise can be complicated by variations in initial effluent temperature and delays caused by the thermal mass of the sensor. Applicant has devised apparatus and methodologies to overcome those complications.

The following examples are illustrative of the apparatus and methodology:

Example 1

A basic sensor 20 was created using a piece of copper 26 with a slit 27 cut in it for the AD 590 thermistor 22 to sit in. It was then electrically insulated with kapton tape and wound with Nichrome wire to be used as the heater 24. Those components were covered in a two-part epoxy in order to water- and F.O.G.-proof the unit, hold everything in place, and thermally insulate most of the unit except for the exposed probe end 30 of the copper. The probe end 30 lets heat escape in order to test how fast the surrounding media can absorb it. By keeping the exposed area relatively small, the heater also can stay small.

For this experiment, the Nichrome wire segment has a resistance of approximately 45 ohm and it is run at 5V dc, giving a power output of approximately 0.56 watt. When capturing data, 5 seconds were allowed to elapse before turning on the power supply to the nichrome wire to ensure that data would be captured correctly. The order of events during the experiment is as follows:

t=0: start recording, ensuring that everything is transmitting properly
    t=5 seconds: turn on heating element
    t=95 seconds: turn off heating element
    t=185 seconds: stop recording Throughout all starting temperature categories that were tested, the probe temperature increased by 15 degrees Celsius in F.O.G. and between 6 and 10 degrees Celsius in water.

Example 2

The test was run again using different power outputs to see what the optimal heat production is, as well as testing different housings. The purpose of this experiment is to try to find out what power output would work best to differentiate between F.O.G. and water. All tests were done on water and F.O.G. that were at around room temperature and only the voltage was changed. Since the internal resistance of the heater remained constant, power increases with the square of voltage. The same timing as in the last experiment was used. The resulting data are shown in FIGS. 4 through 9.

These tests show that although the higher the power output, the greater the temperature difference between the F.O.G. and water rises to become, the rises in temperature for both F.O.G. and water are almost identical through around the 20 second mark, regardless of the power applied to the heater.

Example 3

Tests were run to determine whether or not a difference could be made if the sensor was heated at 2 W for 5, 10, and 15 seconds. The temperature curves looked more or less identical. However, it was learned that even with insulators making up most of the mass of the sensor, it is better to keep the insulator as small as possible to keep a low thermal mass, as reducing the mass also reduces the amount the sensor needs to be heated.

In further testing, an external heating element was turned on for 5 minutes to raise the starting temperature of the fluid being tested. Thirty seconds were given between heating and testing to allow temperatures to stabilize before starting the experiment again.

Due to the nature of the automation, actual temperature readings were not taken to relate the raw data out to temperature. However, it is known that datum 241 of the raw data (vertical scale numbers on FIG. 4 through 10B) correlates to 46 degrees C., and 270 correlates with 52 degrees C. The graph is linear enough to show an accurate representation of what is happening over small temperature changes. At similar temperatures, water and F.O.G. heat up approximately the same amount during the first 20 seconds and vary greatly after that. A more reliable reading uses a ratio of D1/D2, where D1 is the measured difference between start and after 20 seconds have elapsed and D2 is the measured difference between 20 seconds to 60 seconds have elapsed. D2 has very consistently been approximately 50% of D1 when measuring in F.O.G. and between 15% and 25% of D1 when measuring in water.

The following table shows measured D1, D2, and percent change for above graphed temperature curves:

| Water | | | F.O.G. | | |
| --- | --- | --- | --- | --- | --- |
| D1 | D2 | % | D1 | D2 | % |
| 53 | 12 | 22.64% | 44 | 24 | 54.55% |
| 51 | 11 | 21.57% | 42 | 22 | 52.38% |
| 50 | 10 | 20.00% | 41 | 20 | 48.78% |
| 47 | 10 | 21.28% | 40 | 19 | 47.50% |
| 45 | 10 | 22.22% | 38 | 20 | 52.63% |

-continued

| Water | | | F.O.G. | | |
|---|---|---|---|---|---|
| D1 | D2 | % | D1 | D2 | % |
| 44 | 9 | 20.45% | 36 | 19 | 52.78% |
| 43 | 9 | 20.93% | 36 | 18 | 50.00% |
| 43 | 9 | 20.93% | 34 | 18 | 52.94% |
| 42 | 9 | 21.43% | 34 | 17 | 50.00% |
| 40 | 10 | 25.00% | | | |
| 41 | 7 | 17.07% | | | |
| 40 | 8 | 20.00% | | | |
| 39 | 8 | 20.51% | | | |
| 39 | 8 | 20.51% | | | |
| 38 | 7 | 18.42% | | | |
| 39 | 7 | 17.95% | | | |
| 36 | 8 | 22.22% | | | |
| 37 | 7 | 18.92% | | | |
| 36 | 7 | 19.44% | | | |
| 37 | 7 | 18.92% | | | |
| 37 | 7 | 18.92% | | | |
| 33 | 6 | 18.18% | | | |
| 33 | 5 | 15.15% | | | |
| 32 | 5 | 15.63% | | | |

Figure 14A:
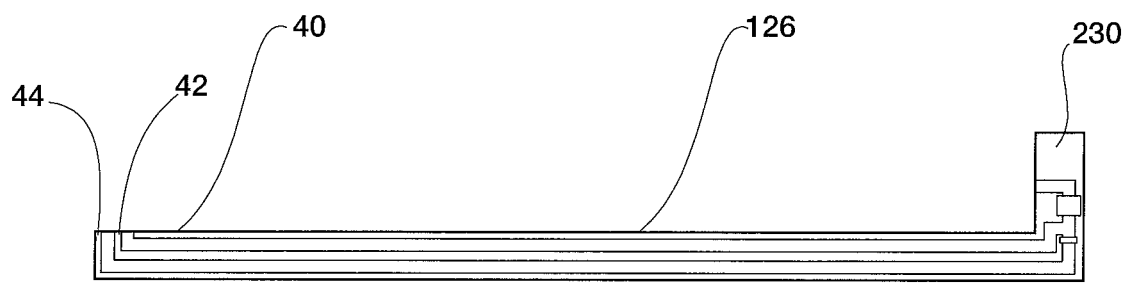
FIG. 14a is a view of another embodiment of PC board usable in the invention.

FIG. 14a shows another printed circuit board 126 design usable in the invention. The wire layout has 3 traces in order to minimize thermal mass and size. This embodiment has a common ground for both the heating element and the thermistor but a common voltage could be used for both, with separate grounds. The common ground version for the thermistor and resistor can operate on separate voltages. The common voltage variation might be better for production in combination with a transistor to power on and off the heater, since transistors usually only work on the ground line as a higher voltage is typically needed to open the gate terminal.

Figure 14B:
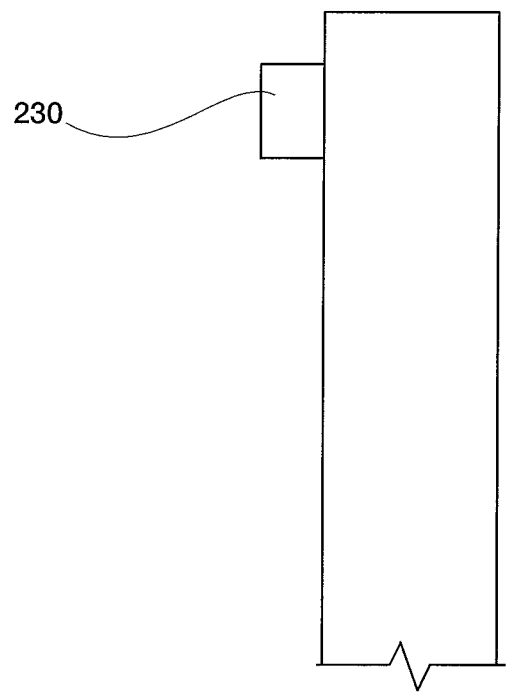
FIG. 14b is a partial side view of the sensor unit made with the PC board embodiment shown in FIG. 14.

This embodiment uses a 24 ohm resistor for the heating element on 3V giving 0.375 watts of heat, which gives a discernible difference between curves for F.O.G. and water. Assuming the sensor will eventually run off of 12V, a 380 ohm resistor would be a good choice to get around the same wattage. This embodiment has an NTC thermistor with 100 k ohms at room temperature. A 100 k ohm resistor gives a high accuracy at room temperature range but not at high temperatures. When used with a 50 k ohms resistor, the sensor seems to be able to read all relevant temperature ranges. This embodiment provides a low profile, ease of assembly, and low thermistor cost. The PCB is roughly 0.25 inches wide. Smaller sizes work better than larger sizes in order to reduce thermal mass. FIG. 14b shows the encapsulated PCB with the exposed heat sink segment 230. A hot glue can be used to act as an electrical insulator. The hot glue seems to easily conduct the heat to a much larger surface area, allowing for an overall cooler sensor and is not the thermal insulator that was expected.

Figure 14C:
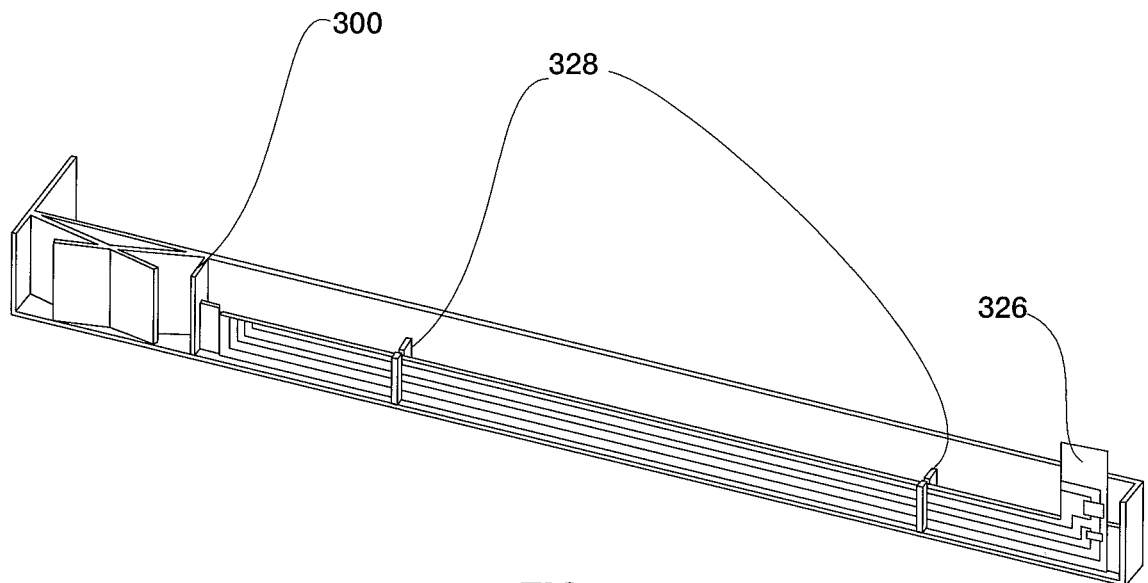
FIG. 14c is perspective view of a jig for receiving the PC board embodiment shown in FIG. 14, partially broken away.

FIG. 14c shows a jig or housing 300 for the PCB 325. The jig holds the PCB with its attached resistor and thermistor in place during encapsulation with a hot glue or potting compound. This allows for enough space to pot the board and mounted components without risking the possibility of having a lack of potting material or air bubbles. The board 326 can be positively held in place so that there is no way it is put in wrong and having it misaligned. The PCB 326 is held in place with spacers 328.

Figure 15:
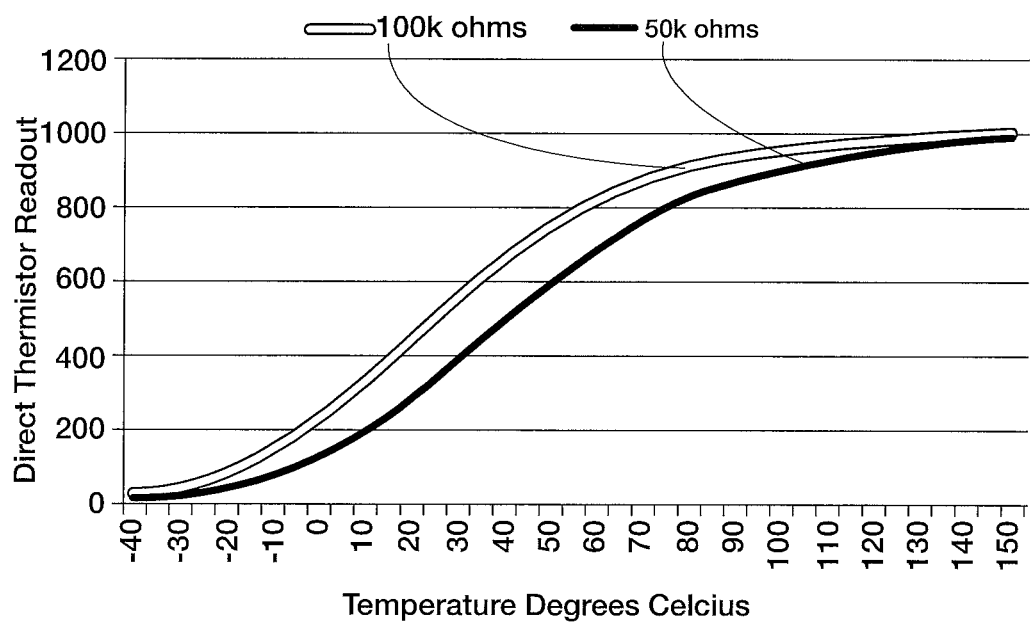
FIG. 15 is a graph of temperature rise over time for oil and water using the PC board embodiment shown in FIGS. 14a-c.

The graph of FIG. 15 shows what the thermistor reads at various temperatures. The optimal measuring range is where the line graphed is relatively flat. The 100 k ohm line is more accurate in the lower temperatures and even below freezing while the 50 k ohm line becomes accurate toward freezing and stays accurate for longer.

A suitable potting material is 823C Epoxy from MG Chemicals. The epoxy is chemically resistant, waterproof, and can cure at room temperature. The potting compound performs a few basic functions in the sensor. It holds everything in place, electrically insulates the traces, and makes it so that the environment cannot harm the sensor. Lastly, it helps act as a thermal insulator and therefore decreases the thermal leakage in undesired directions.

Figure 16:
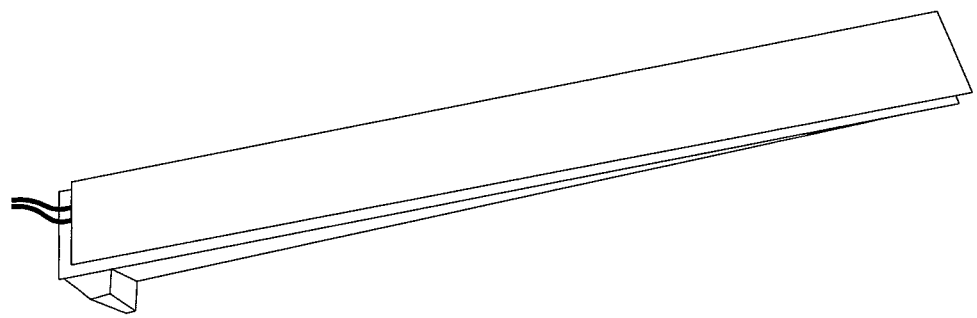
FIG. 16 is a view of another embodiment with a tape form of encapsulation.

Another embodiment shown in FIG. 16 uses an encapsulation tape 370 instead of (or perhaps in addition to) a potting compound or hot melt. In this embodiment the PCB is sandwiched within layers of VHB tape or similar adhesive. VHB tape is available from 3M, St. Paul, Minn. An advantage of the VHB embodiment is the ease of assembly and not having to wait for any curing process before further assembly, packaging, or shipping. It might be possible to have the probe end inside and to probe through the VHB, similar to what was done with the hot glue on the above experiment. In the embodiment shown in FIG. 16, there are 3 layers of VHB tape: a base layer, two strips on either side of the PCB, and a top layer with the backing still on it.

Figure 17:
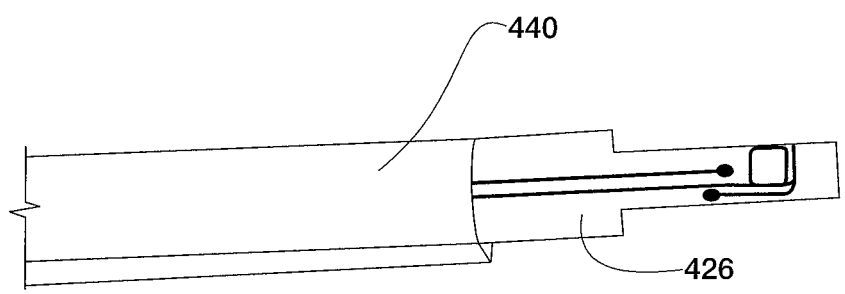
FIG. 17 shows a stage of assembly of yet another form of encapsulation of a sensor unit.
Figure 18:
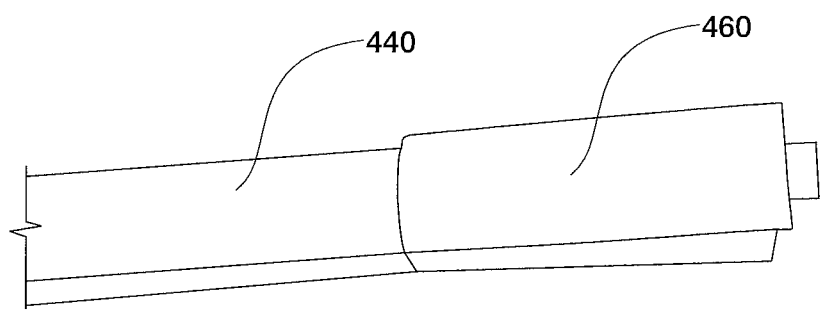
FIG. 18 show the final sensor unit of the embodiment of FIG. 17.

Another encapsulation technique is shown in FIGS. 17 and 18. This uses a tube 440 and a sleeve-like cap 460. A slit in the tube pipe and a groove in the cap hold the PCB 426 in place. Silicone is put into the tube 440 with the PCB to seal the base of the PCB into the tube 440 and provide a seal for potting. The cap 460 is applied. After the Silicone cures, epoxy poured into the cavity in the end of the tube 440 and cap 460 to fill it the space from the silicone to the brim of the cap 460.

As noted, the sensor unit is deployed in a liquid, and the task is to determine if the liquid is of one layer of stratification or another. Other ways to use the data can also be used to make this determination. For example, the area under the curves of the data depicted in the graphs for a given period of time can be computed and compared with other collected data, such as stored data. Averages of the temperature values over the set period can also be computed and such comparisons made from the computed averages.

Figure 20:
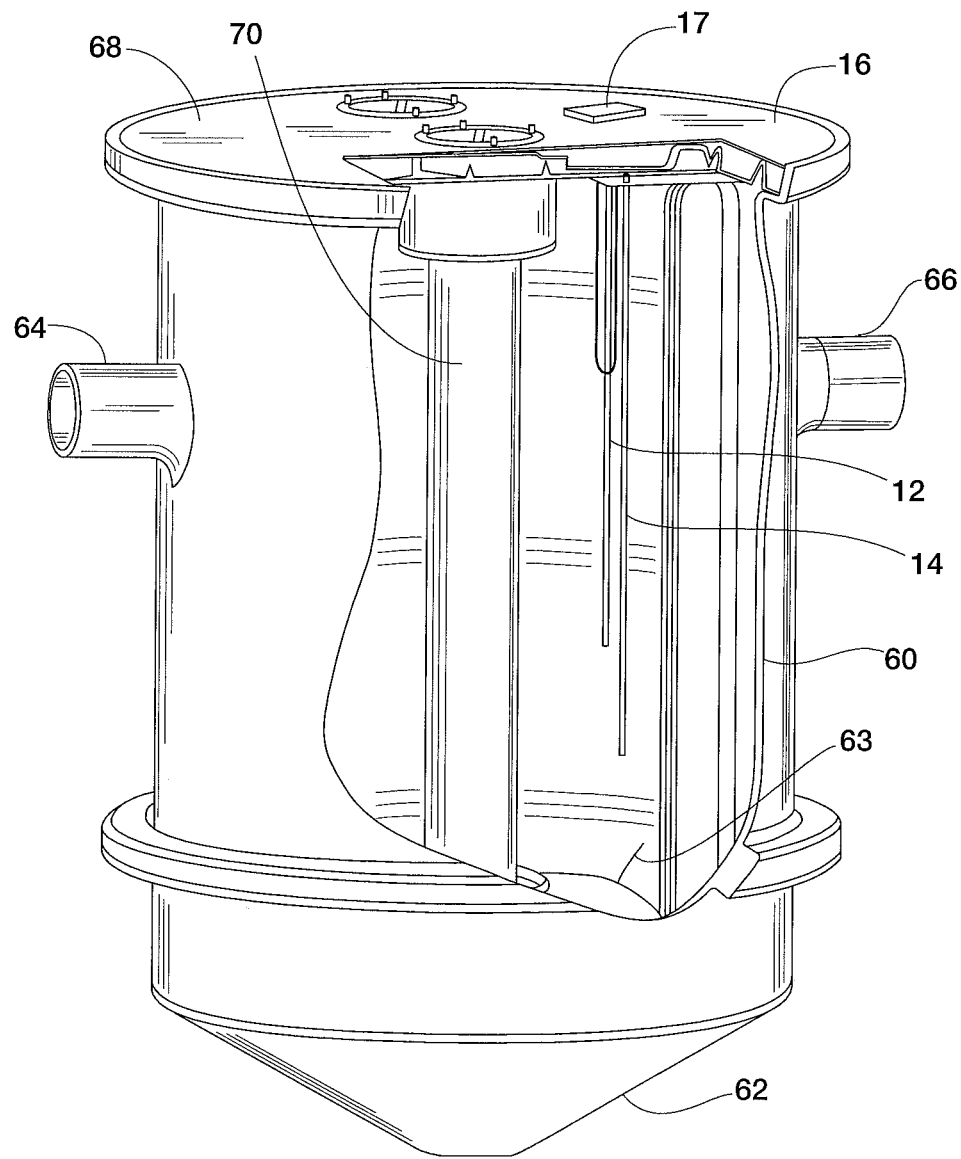
FIG. 20 shows a grease trap equipped with a sensor in accordance with an embodiment of the invention.

An embodiment provides the sensors positioned at differing heights in a grease trap tank or other passive separator, such as Thermaco's Trapzilla® grease trap, shown in FIG. 20. The grease trap includes a tank 60 having a conically shaped bottom 62. A divider 63 divides the tank 60 into an upper chamber and a lower chamber. A hole (not shown in FIG. 20) near an upper part of the divider 63 allows F.O.G. to rise into the upper chamber. An inlet invert 64 in the tank receives incoming waste water that includes F.O.G., while an outlet invert 66 removes grey water from the tank. The F.O.G. stays in the tank and rises through the hole in the divider 63 to collect as a grease mat above the divider. A lid 68 covers the tank. A pipe 70 extends through the lid, upper chamber, and the divider 63 for pumping solid waste out of the lower chamber, as well as the F.O.G. Most of the grey water passes through the outlet invert 66 during normal kitchen effluent flows.

Rods 12 and 14 are supported by lid 68 and each have a sensor as described above near their bottoms. The remainder of the column lengths of the rods can be made up of conduit for carrying wires to the top and for supporting the sensor at the correct depth within the tank. Rods 12, 14 are of differing length, and the sensors each indicate whether water or FOG is present at its height within the tank. When the F.O.G. capacity of the tank is approaching, attached electronics can generate a signal to call for pumping the F.O.G. from the tank. The longer rod 14 preferably terminates at the level where the tank is considered to be 75% full of F.O.G., and the shorter one is at the 50% level. Other locations in the tank can be used.

Figure 19:
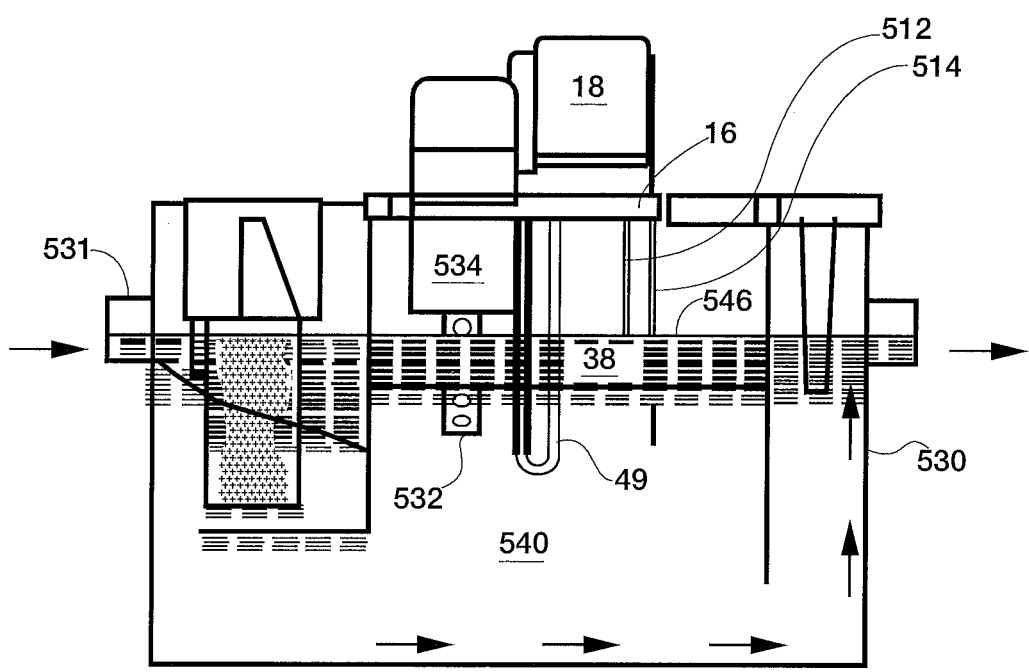
FIG. 19 shows a skimmer apparatus equipped with a sensor in accordance with an embodiment of the invention.

The sensors can also be used with active separators that do skimming, such as Thermaco's Big Dipper® separators shown in FIG. 19. As used in this application, "skimming" includes other ways of taking the F.O.G. off the top, including opening spouts that drain the F.O.G. (see U.S. Pat. No. 7,186,346 for examples), pumping the F.O.G. (see U.S. Pat. No. 6,517,715 for an example), or other active methods.

The thermistors are useful on the active F.O.G. removal units, such as the Big Dipper. As seen in FIG. 19, such active unit includes a container 530 that receives effluent from an inlet 531 and allows the flow rate to slow sufficiently that a F.O.G. mat 38 can collect on top of the grey water 540. The active unit has one or more rotating disks 532 formed of a plastic or like material to which F.O.G. contaminants are attracted. Typically, the rotation of the disk is in an at least partially immersed condition, which allows the F.O.G. 546 that floats on grey water 540 to cling to the disk so that it is removed from the body of water upon rotation of the disk through wipers 534 that scrape the F.O.G. from the disk and channel the F.O.G. to a collection or disposal storage unit. Examples of such units are seen in U.S. Pat. Nos. 7,208,080, 7,186,346, and 6,491,830, all commonly assigned with this application and the relevant disclosures of which are hereby incorporated by reference.

Figure 21:
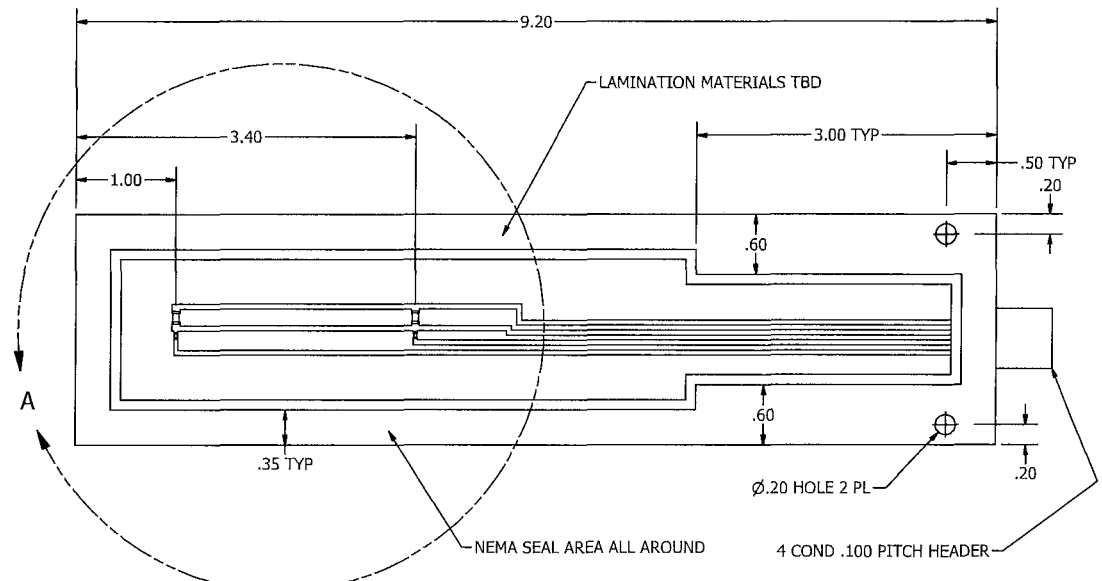
FIG. 21 shows an alternate embodiment of a sensor.

FIG. 21 shows an alternate embodiment of a sensor. In this sensor two levels of a liquid can be evaluated with a single sensor. The sensor as shown is intended to be mounted with its longer sides extending vertically in the container for the liquids. That positions the two thermistors and two resistors at differing heights, so that the data available is more extensive. The resistors, thermistors and connection traces are printed on a sheet of a plastic material and covered by an electrical insulator in the form of another sheet of plastic. The sheets are thin, so the heat flows out from the resistor over a thermal path through the surrounding plastic to the surrounding liquid. The thermistor temperature is the result of conduction through the materials between it and the resistor, but with the heat diverted to the surrounding liquid affecting how much heat travels to the thermistor. The greater the heat transfer through the plastic sheets to the surrounding liquid, the lower the temperature of the thermistor will be. The resistors can both be supplied with current using a common conductor and a common ground. The thermistors also share the same common ground but each has a separate supply current, so that each thermistor can be read individually.

Figure 22:
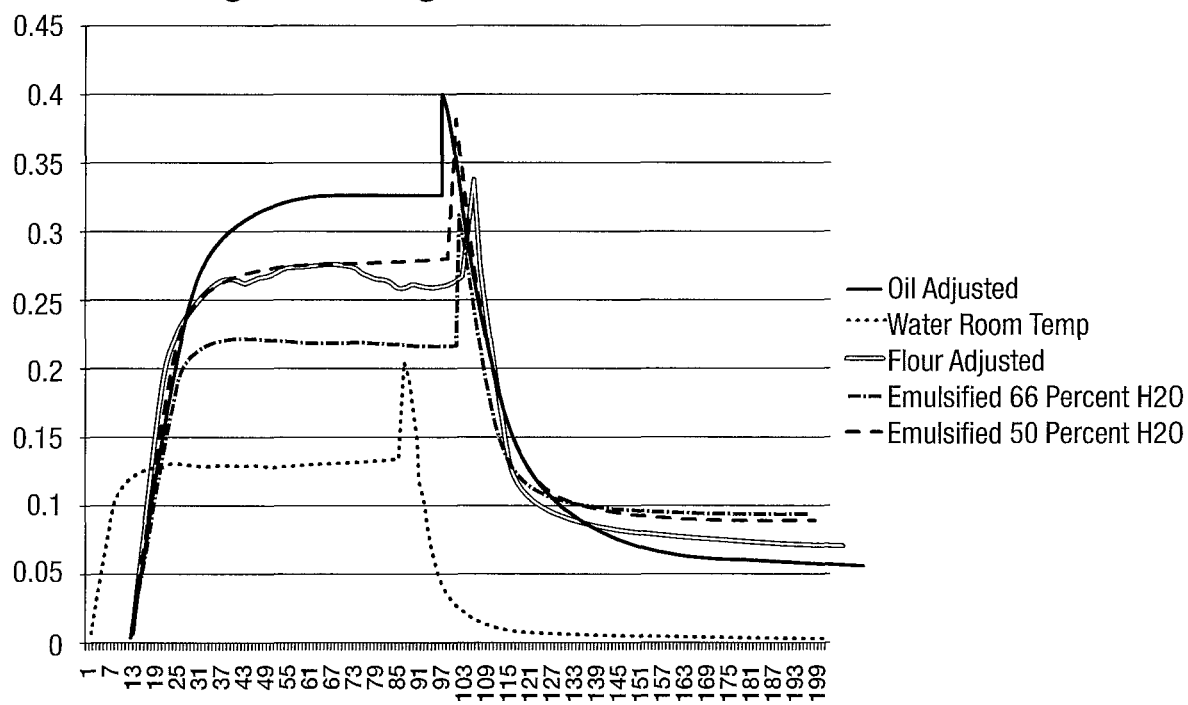
FIG. 22 shows a graph of temperature versus time for various FOG and water combinations as sensed using the sensor of FIG. 21.

FIG. 22 shows a graph of temperature versus time for various FOG and water combinations as sensed using the sensor of FIG. 21. As can be seen, various types of liquid mixtures that may be encountered in a grease trap or an active skimmer can be sensed, and the data collected can determine which of the types of mixtures are present. These mixtures include FOG (oil), room temperature water, water containing flour, water emulsified with FOG in a mixture of 66% water, and water emulsified with FOG in a mixture of 50% water.

Certain modifications and improvements will occur to those skilled in the art upon reading the foregoing description. It should be understood that all such modifications and improvements have been omitted for the sake of conciseness and readability, but are properly within the scope of the following claims.

What is claimed is:

1. An apparatus for discriminating between liquids having differing thermal conductivities comprising data gathering equipment,
   a source of electricity,
   a thermally conductive substrate,
   a resistor mounted to the thermally conductive substrate with two leads to the source of electricity to enable a current to be passed through the resistor from time to time to generate heat,
   a thermistor mounted to the substrate with two leads to enable a current to be passed through the thermistor to the data gathering equipment to generate data indicative of thermistor temperature to determine the change of thermistor temperature over time, and to use the change in thermistor temperature over time to determine in which of two liquids having differing thermal conductivities the substrate, resistor and thermistor are immersed, and
   an electrical insulator encapsulating the resistor, the thermistor and at least part of the thermally conductive substrate.

2. The apparatus as claimed in claim 1 wherein the leads of the resistor and thermistor are electrically connected to electrically conductive regions of the thermally conductive substrate.

3. The apparatus as claimed in claim 1 wherein one lead of the resistor and one lead of the thermistor are both electrically connected to a common electrically conductive region of the thermally conductive substrate.

4. The apparatus as claimed in claim 1 wherein the substrate is a printed circuit board with a metal face.

5. The apparatus as claimed in claim 4 wherein the metal face is copper.

6. The apparatus as claimed in claim 4 wherein the metal face is copper coated with gold.

7. The apparatus as claimed in claim 1 wherein the electrical insulator is a potting compound.

8. The apparatus as claimed in claim 1
   wherein the leads of the thermistor that are connected to the data gathering equipment samples the data indicative of thermistor temperature over a period of at least forty seconds and computes a ratio of temperature change, the denominator of the ratio being the temperature change in a first part of the period and the numerator of the ratio being the temperature change in a second part of the period after the first part.

9. The apparatus as claimed in claim 1 further comprising a thermal paste between the thermally conductive substrate and the resistor and thermistor.

10. The apparatus as claimed in claim 1 wherein a portion of the thermally conductive substrate extends beyond the electrical insulator to provide a thermal path from the resistor and thermistor to a liquid in which the apparatus may be immersed.

11. An apparatus for discriminating between liquids having differing thermal conductivities comprising
    data gathering equipment,
    a source of electricity,
    a thermally conductive substrate, a resistor mounted to the substrate with two leads to the source of electricity to enable a current to be passed through the resistor for a period of time to generate heat, a thermistor mounted to the substrate with two leads to enable a current to be passed through the thermistor to the data gathering equipment to generate data indicative of thermistor temperature to determine the change of thermistor temperature over time, and to use the data indicative of the change in thermistor temperature over time to determine in which of two liquids having differing thermal conductivities the substrate, resistor and thermistor are immersed, and wherein one lead of the resistor and one lead of the thermistor are both electrically connected to a common region conductor of the mounted on the thermally conductive substrate with thermal paste between the substrate and the resistor and thermistor, an electrical insulator encapsulating the resistor, the thermistor and at least part of the substrate, and wherein the leads of the thermistor are connected to a data gathering equipment that samples the data indicative of thermistor temperature over a period and computes a ratio of temperature change, the denominator of the ratio being the temperature change in a first part of the period and the numerator of the ratio being the temperature change in a second part of the period after the first part.

12. A separator for separating F.O.G. from an effluent that contains F.O.G. and water comprising
a tank,
an inlet to the tank for receiving effluent that contains F.O.G. and an outlet to allow grey water to leave the tank, the tank having a size to enable stratification to form a layer of F.O.G. in the tank on top of water in the tank,
data gathering equipment,
a source of electricity, and
a sensor apparatus at a location within the tank for discriminating between F.O.G. and water at the location in the tank including a thermally conductive substrate, a resistor mounted to the thermally conductive substrate with two leads to the source of electricity to enable a current to be passed through the resistor for a period of time to generate heat, a thermistor mounted to the substrate with two leads to enable a current to be passed through the thermistor to the data gathering equipment to generate data indicative of thermistor temperature to determine the change of thermistor temperature over time, and to use the data indicative of the change in thermistor temperature over time to determine in which of F.O.G or water the substrate, resistor and thermistor are immersed, and
an electrical insulator encapsulating the resistor, the thermistor and at least part of the thermally conductive substrate.

13. A separator for separating F.O.G. from an effluent that contains F.O.G. as claimed in claim 12 wherein the separator has a skimmer and control system that acts on the sensed data to determine when to skim.

14. A separator for separating F.O.G. from an effluent that contains F.O.G. as claimed in claim 12 wherein the tank has a defined capacity for holding F.O.G. and a first rod positions a sensor apparatus at a level where the tank is considered to be at a first percentage of the defined capacity, and a second rod positions a sensor apparatus at a level where the tank is considered to be at a second percentage of the defined capacity.

15. A method of discriminating between liquids having differing thermal conductivities comprising
positioning a sensor at a location where the sensor may be exposed to the liquids having differing thermal conductivities,
the sensor including a thermal path from a heater and a thermistor,
applying heat to the sensor with the heater for a period of time,
reading data from the thermistor indicative of thermistor temperature repeatedly over a period of time to determine the change of thermistor temperature over time, and
computing a ratio of the thermistor temperature change in a first part of the period of time and the thermistor temperature change in a second part of the period of time after the first part of the period of time.

16. A method as claimed in claim 15 wherein the liquids having differing thermal conductivities are selected from the group consisting of lipids and water; petroleum oils and water; and concentrated alcohols and water.

17. A method of discriminating between liquids having differing thermal conductivities comprising
positioning a sensor at a location where it may be exposed to the liquids having differing thermal conductivities,
the sensor including a thermal path from a heater and a thermistor,
applying heat to the sensor with the heater for a period of time,
reading data from the thermistor indicative of thermistor temperature repeatedly over a period of time to determine changes in thermistor temperature over the period of time, and
comparing values of the data that was read from the thermistor with pre-stored values of temperature variations with time for the liquids to determine if the sensor is in one liquid or another.

18. The method of claim 17 in which reading data includes computing a value for an area under a curve of temperature change with time, and
comparing the computed value for an area with known values for the area for the liquid.

19. A method as claimed in claim 17 wherein the liquids having differing thermal conductivities are selected from the group consisting of lipids and water; petroleum oils and water; and concentrated alcohols and water.

20. A method of discriminating between liquids having differing thermal conductivities as claimed in claim 15 wherein computing a ratio of temperature change is computing a ratio of temperature rises.

* * * * *